US 8,293,865 B2

(12) United States Patent
Lin et al.

(10) Patent No.: US 8,293,865 B2
(45) Date of Patent: Oct. 23, 2012

(54) PHOSPHORUS-CONTAINING COMPOUNDS AND THEIR PREPARATION PROCESS AND USE

(75) Inventors: Ching-Hsuan Lin, Taichung (TW); Tsung Li Lin, Taichung (TW); Yu-Ting Fang, Taichung (TW); Kuen-Yuan Hwang, Hsinchu County (TW); An-Pang Tu, Hsinchu County (TW)

(73) Assignees: Chang Chun Plastics Co., Ltd., Hsinchu County (TW); National Chung Hsing University, Taichung (TW)

( * ) Notice: Subject to any disclaimer, the term of this patent is extended or adjusted under 35 U.S.C. 154(b) by 572 days.

(21) Appl. No.: 12/458,186

(22) Filed: Jul. 2, 2009

(65) Prior Publication Data

US 2010/0004426 A1    Jan. 7, 2010

(30) Foreign Application Priority Data

Jul. 2, 2008   (TW) ................ 97124888 A

(51) Int. Cl.
*C08G 79/02* (2006.01)
*C08G 79/00* (2006.01)
*C07C 9/02* (2006.01)

(52) U.S. Cl. ........ 528/399; 528/299; 528/310; 528/287; 558/73; 558/87

(58) Field of Classification Search .............. 558/73, 558/87; 528/399, 299, 310, 287
See application file for complete search history.

(56) References Cited

U.S. PATENT DOCUMENTS 6,984,716 B2   1/2006 Hwang et al.

2004/0077825 A1   4/2004 Hwang et al.
2006/0247343 A1  11/2006 Kishimoto et al.

FOREIGN PATENT DOCUMENTS

CN   1846019       10/2006
EP   1 889 878 A1   2/2008
(Continued)

OTHER PUBLICATIONS

Office Action and Search Report issued by the Taiwan Patent Office in the corresponding Taiwan Patent Application No. 097124888 (5 pages).

(Continued)

*Primary Examiner* — Duc Truong
(74) *Attorney, Agent, or Firm* — Stites & Harbison, PLLC; Juan Carlos A. Marquez, Esq.

(57) ABSTRACT

A series of novel phosphorus-containing compounds having the following formula is provided:

(I)

in which:
$R_1$-$R_4$, A, Q and m are as defined in the specification.
A process for the preparation of the compound of formula (I) is also provided. A polymer of formula (PA), and preparation process and use thereof are further provided. A polymer of formula (PI), and preparation process and use thereof are also provided.

2 Claims, 7 Drawing Sheets

FOREIGN PATENT DOCUMENTS

TW 498084 8/2002

OTHER PUBLICATIONS

Chun Shan Wang et al., "Synthesis and Properties of Phosphorus-Containing PEN and PBN Copolyesters"; Polymer vol. 40(1999); pp. 747-757.

C.H. Lin et al., "Novel Phosphorus-Containing Epoxy Resins Part I. Synthesis and Properties"; Polymer vol. 42(2001); pp. 1869-1878.

C.H. Lin et al., "Synthesis and Properties of Phosphorus-Containing Advanced Epoxy Resins, II"; Journal of Applied Polymer Science vol. 78(2000); pp. 228-235.

Ching Hsuan Lin et al., "Synthesis and Property of Phosphorus-Containing Bismaleimide by a Novel Method"; Journal of Polymer Science: Part A: Polymer Chemistry, vol. 38(2000); pp. 2260-2268.

Ying-Ling Liu et al., "Synthesis and Properties of New Organosoluble Aromatic Polyamides With Cyclic Bulky Groups Containing Phosphorus"; Polymer vol. 43(2002); pp. 5757-5762.

Chuan Shao Wu et al., "Synthesis and Characterization of New Organosoluble Polyaspartimides Containing Phosphorus"; Polymer vol. 43(2002); pp. 1773-1779.

Ying Ling Liu et al, "Flame-Retardant Epoxy Resins From O-Cresol Novolac Epoxy Cured With a Phosphorus-Containing Aralkyl Novolac"; Journal of Polymer Science: Part A: Polymer Chemistry vol. 40(2002); pp. 2329-2339.

I.K. Varma et al., "Polyimides. I. Preparation and Properties of Phosphorus-Containing Polyimides"; Journal of Applied Polymer Science vol. 28(1983); pp. 2805-2812.

John W Connell et al., "Space Environmentally Stable Polyimides and Copolyimides Derived From bis(3-aminophenyl)-3,5-di(trifluoromethyl)phenylphosphine oxide"; High Performance Polymers vol. 13(2001); pp. 23-34.

Kent A. Watson et al., "Space Environmentally Stable Polyimides and Copolyimides Derived From [2,4-Bis(3-aminophenoxy)phenyl]Diphenylphosphine Oxide"; Macromolecules vol. 35(2002); pp. 4968-4974.

PHOSPHORUS-CONTAINING COMPOUNDS AND THEIR PREPARATION PROCESS AND USE

FIELD OF THE INVENTION

The present invention relates to phosphorus-containing compounds and preparation process and use thereof, and particularly to compounds deriving from phosphorus-containing diphenol (HPP) and preparation process thereof. The derivatives thereof can be further used for synthesis of polymer materials such as polyamides and polyimides.

DESCRIPTION OF THE PRIOR ART

Traditionally used flame resistant compositions generally contain flame resistant materials such as halogen containing compounds or oxidants containing antimony or vanadium as components to form a high thermal resistant composition, and use of these materials often causes severe environmental contamination problems. For example, bromine containing epoxy resins are particularly useful in flame resistant electronic materials, but release corrosive and toxic substances such as hydrogen bromide, dibenzo-p-dioxin and dibenzofuran in combustion. In addition to the halogen containing compounds, another flame retardant approach is coating an additional non-flammable layer outside the plastics, with phosphorus-containing compounds being most preferred with respect to efficiency. For example, phosphorus-containing compound 9,10-dihydro-9-oxa-10-phosphaphenanthrene 10-oxide (DOPO) has active hydrogen atoms capable of reacting with electron deficient compounds such as benzoquinone[1], oxirane[2], maleic acid[3], bismaleimide[4], diaminobenzophenone[5-6], and terephthaldicarboxaldehyde [7], and derivatives thereof have gained extensive attention from academic and industrial circles. Derivatives of DOPO can be used as raw materials for polymer materials such as epoxy resins, polyamides or polyimides.

Taiwan Patent No. 498084 discloses a method for synthesizing phosphorus-containing diphenol (HPP), in which the more expensive non-halogen phosphorus-containing flame resistant agent (DOPOBQ), which is synthesized from DOPO and benzoquinone[1], is successfully replaced by cheaper HPP. This invention further discloses a method for synthesizing HPP derivatives which can be used as raw materials for polymer materials such as epoxy resins, polyamides or polyimides. The HPP and DOPOBQ have the following structures:

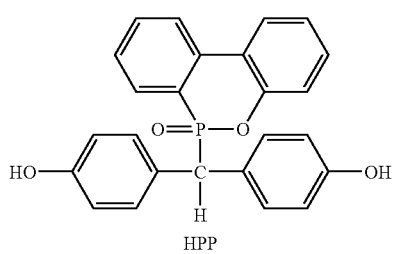

HPP

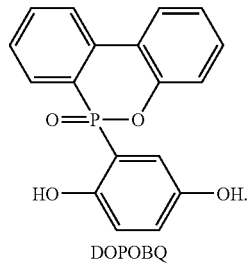

DOPOBQ

Common aromatic polyimide films with high molecular weight generally have advantages such as tenacity, flexibility, solvent resistance, a high glass transition temperature (Tg) and better thermal stability. However, polyimide films generally have a color between yellow and amber, and thus have high light absorption. Some research indicates that the formation of charge-transfer complex (CTC) will cause the color of polyimide films to be deepened. Use of aromatic diamine having bulky group can effectively lower the formation of CTC, thereby causing the color of polyimide films to become pale.

Varma et al. synthesized a polyimide having a structure of polyphenyleneoxide (PPO)[8]. However, the formation of CTC could not be effectively inhibited because the incorporated PPO group was not bulky enough; therefore, the polyimide containing PPO still had too dark a color. In 2001, Connell et al. developed a novel diamine having PPO group [9], and used the diamine as a raw material and a series of dianhydrides to synthesize polyimides containing phosphorus in the backbone. However, the polyimide films thus prepared had somewhat higher crispness and poor mechanical properties.

In 2002, Connell et al. synthesized another novel diamine containing phosphorus in the side chain [10], and used the diamine and a series of dianhydrides to synthesize polyimides containing phosphorus in the side chain. Because the incorporation of the bulky phosphorus group in the side chain obviously inhibited the formation of CTC, the polyimides had a paler color; with respect to mechanical properties, all the polyimides formed with anhydride other than pyromellitic dianhydride (PMDA) had tenacity, better mechanical properties, and a glass transition temperature (Tg) ranging from 212 to 251° C. Therefore, the polyimides containing phosphorus in the side chain can lower the color of the film.

The present invention synthesizes a novel diamine containing phosphorus in the side chain, and used the diamine and a series of dianhydrides or diacids to prepare polyamides or polyimides having better transparency and containing phosphorus in the side chain. The resulting phosphorus-containing polymers can be used as flexible printed circuit board materials.

REFERENCES

[1] Wang, C. S.; Lin, C. H. Polymer 1999; 40; 747.
[2] Lin, C. H.; Wang, C. S. Polymer 2001, 42, 1869.
[3] Wang, C. S.; Lin, C. H.; Wu, C. Y. J. Appl. Polym. Sci. 2000, 78, 228.
[4] Lin, C. H.; Wang, C. S. J. Polym. Sci. Part A: Polym. Chem. 2000, 38, 2260.
[5] Liu, Y. L.; Tsai, S. H. Polymer 2002, 43, 5757.
[6] Wu, C. S.; Liu, Y. L.; Chiu, Y. S. Polymer 2002, 43, 1773.
[7] Liu, Y. L.; Wu, C. S.; Hsu, K. Y.; Chang, T. C. J. Polym. Sci. Part A: Polym Chem. 2002, 40, 2329.
[8] Varma, K.; Rao, B. S. J Appl Polym Sci 1983, 28, 2805.
[9] Connell, J. W.; Watson, K. A. High Perform Polym 2001, 13, 23.
[10] Watson, K. A.; Palmeri, F. L.; Connell, J. W. Macromolecules 2002, 35, 4968.

SUMMARY OF THE INVENTION

The present invention provides phosphorus-containing compounds having the following chemical formula:

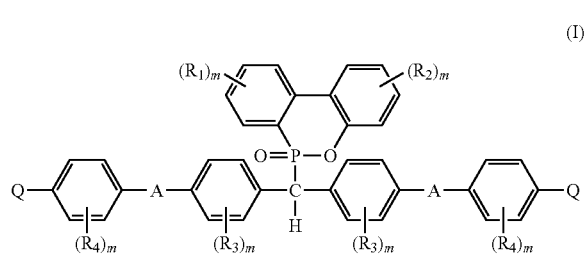
(I)

in which:

$R_1$-$R_4$ are each selected from the group consisting of hydrogen atom, $C_1$-$C_6$alkyl, $C_1$-$C_6$alkoxy, $C_1$-$C_6$haloalkyl, $C_3$-$C_7$cycloalkyl, —$CF_3$, —$OCF_3$, and halogen atom;

A is —O— or

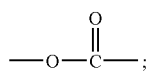

Q is selected from the group consisting of —$NO_2$, —$NH_2$,

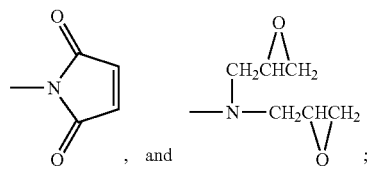

and m is an integer of 1-4.

The present invention also provides a process of preparing the compound of formula (I), which includes reacting an organophosphorous compound of formula (II) with a compound of formula (III) in a solvent in the presence of a catalyst to form the compound of formula (I);

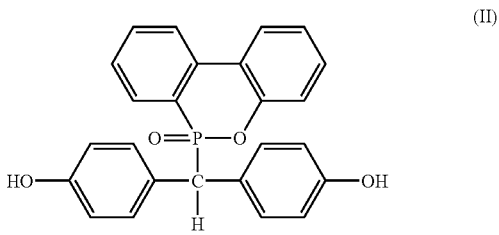
(II)

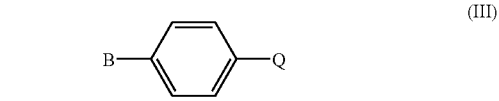
(III)

in which B is halogen or

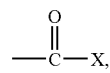

X is halogen, and Q is defined as above.

The present invention also provides a compound of formula (PA) and a process for preparing the same. The present invention further provides a compound of formula (PI) and a process for preparing the same.

DETAILED DESCRIPTION

Figure 1:
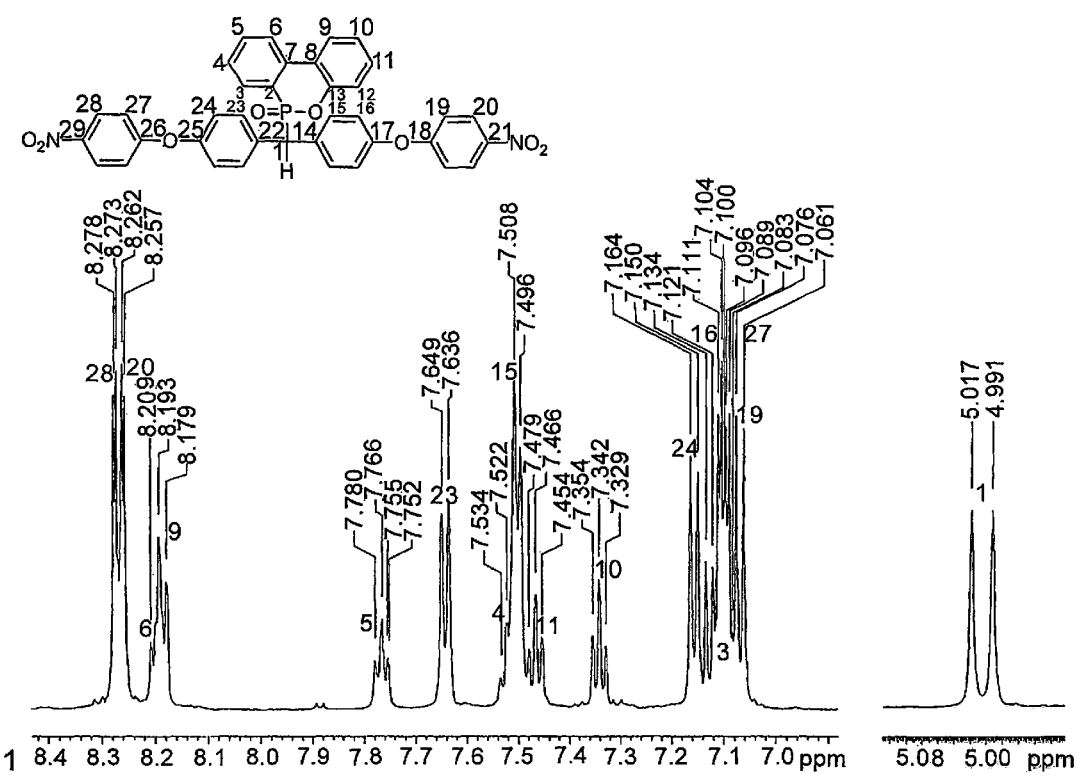
FIG. 1 is a $^1$H NMR spectrum of compound HPP-A.

The present invention is directed to a series of novel phosphorus-containing compounds which can be used as raw materials for polymer materials such as epoxy resins, polyamides and polyimides, and further used in flame resistant materials.

The present invention provides phosphorus-containing compounds having the following chemical formula:

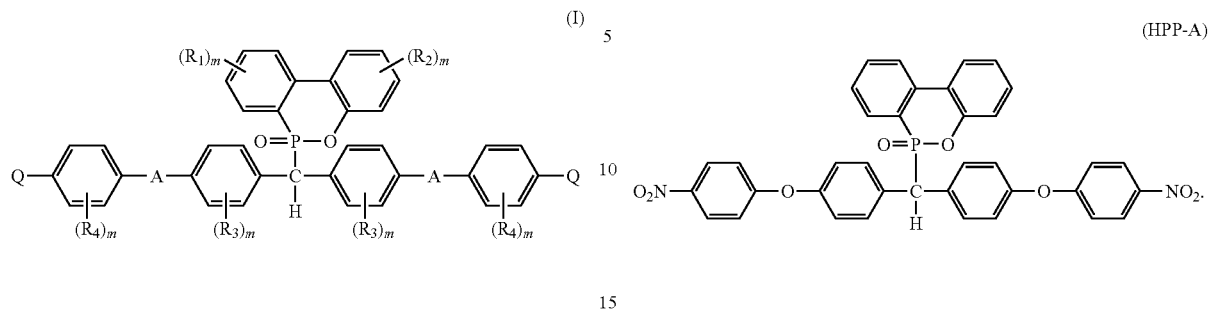

in which:
R$_1$-R$_4$ are each selected from the group consisting of hydrogen atom, C$_1$-C$_6$alkyl, C$_1$-C$_6$alkoxy, C$_1$-C$_6$haloalkyl, C$_3$-C$_7$cycloalkyl, —CF$_3$, —OCF$_3$, and halogen atom;
A is —O— or

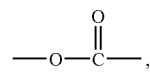

Q is selected from the group consistng of —NO$_2$, —NH$_2$,

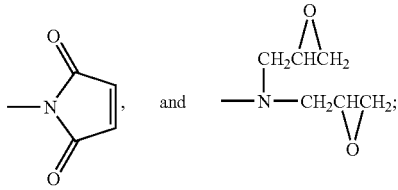

and
m is an integer of 1-4.
When R$_1$-R$_4$ are hydrogen atoms, A is —O—, and Q is —NO$_2$, one embodiment of the compound of formula (I) can have a structural formula of When R$_1$-R$_4$ are hydrogen atoms, A is —O—, and Q is —NH$_2$, one embodiment of the compound of formula (I) can have a structural formula of When R$_1$-R$_4$ are hydrogen atoms, A is

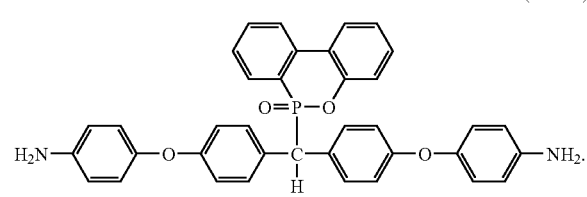

and Q is —NO$_2$, one embodiment of the compound of formula (I) can have a structural formula of

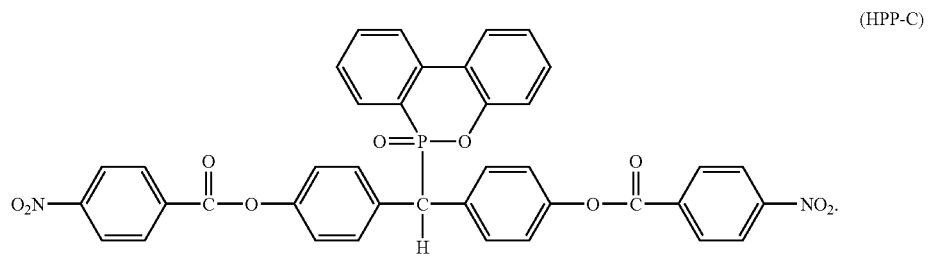

When $R_1$-$R_4$ are hydrogen atoms, A is

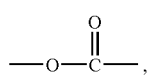

and Q is —$NH_2$, one embodiment of the compound of formula (I) can have a structural formula of

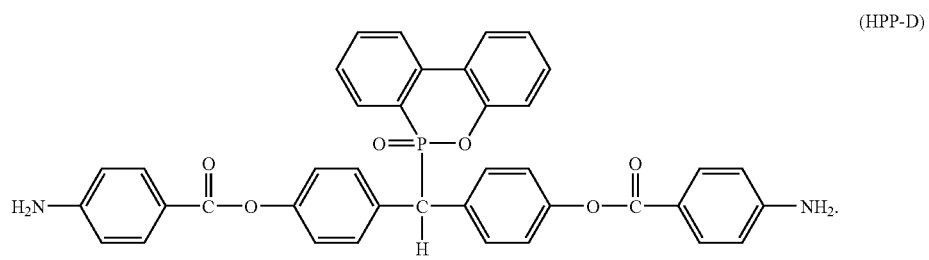

(HPP-D)

When $R_1$-$R_4$ are hydrogen atoms, A is —O—, and Q is

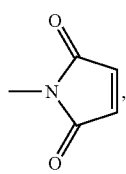

one embodiment of the compound of formula (I) can have a structural formula of

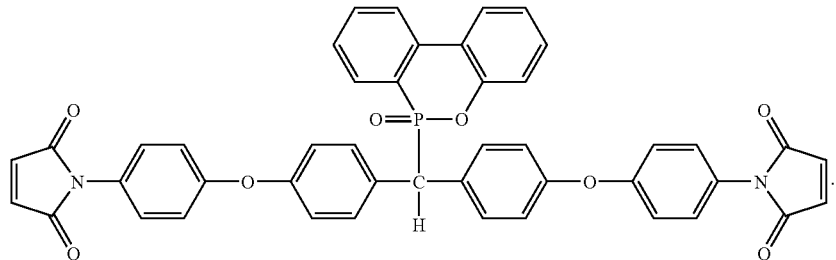

(HPP-E)

When $R_1$-$R_4$ are hydrogen atoms, A is —O—, and Q is

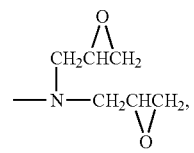

one embodiment of the compound of formula (I) can have a structural formula of

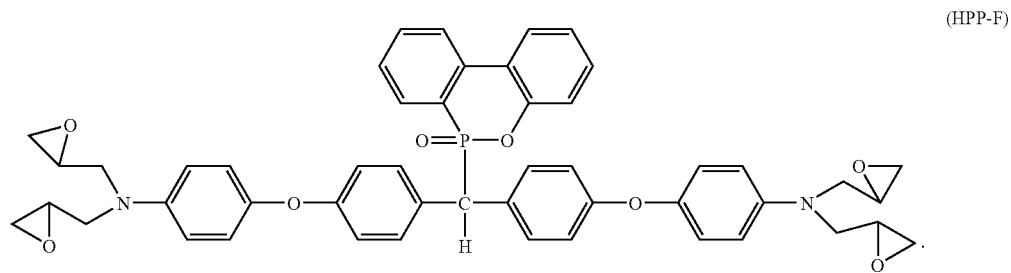
(HPP-F)
When $R_1$-$R_4$ are hydrogen atoms, A is
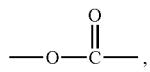
and Q is
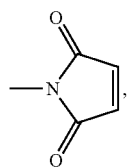
one embodiment of the compound of formula (I) can have a structural formula of
When $R_1$-$R_4$ are hydrogen atoms, A is
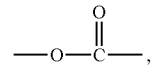
and Q is
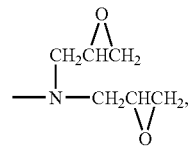
one embodiment of the compound of formula (I) can have a structural formula of
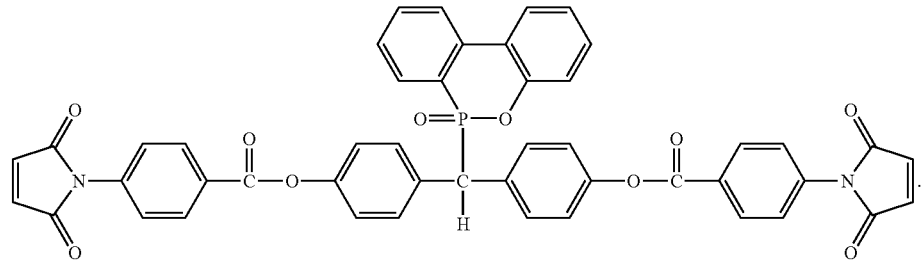
(HPP-G)

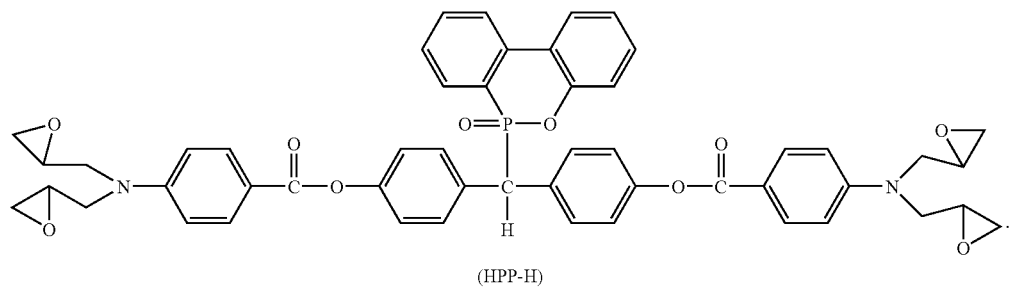

(HPP-H)

The present invention also provides a process of preparing the compound of formula (I), which includes reacting an organophosphorous compound of formula (II) with a compound of formula (III) in a solvent in the presence of a catalyst to form the compound of formula (I);

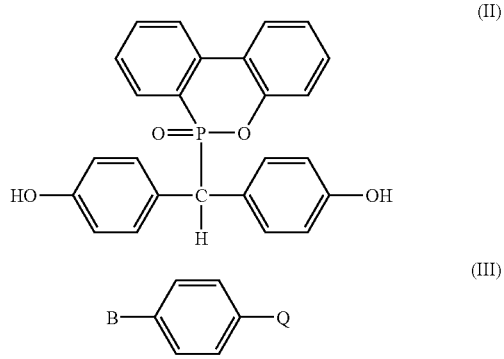

(II)

(III)

in which B is halogen or

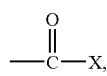

X is halogen, and Q is defined as above.

When $R_1$-$R_4$ are hydrogen atoms, the process above includes:

(a) reacting an organophosphorous compound of formula (II) with a compound of formula (III) where B is a halogen in a solvent in the presence of a catalyst to form the compound of formula (HPP-A) in which A is —O— and Q is —$NO_2$; or (b) repeating step (a) to produce the compound of formula (HPP-A) first, followed by hydrogenation in a solvent to form the product, i.e. compound of formula (HPP-B) in which A is —O— and Q is —$NH_2$; or (c) reacting an organophosphorous compound of formula (II) with a compound of formula (III) where B is

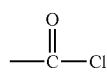

in a solvent to form the compound of formula (HPP-C) in which A is

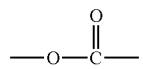

and Q is —$NO_2$; or (d) repeating step (c) to produce the compound of formula (HPP-C) first, followed by hydrogenation in a solvent to form the product, i.e. compound of formula (HPP-D) in which A is

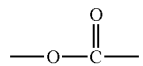

and Q is —$NH_2$.

The process according to the present invention can further include:

(e) after step (b), reacting the compound of formula (HPP-B) with maleic anhydride in a solvent to form the product, i.e. compound of formula (HPP-E) in which A is —O— and Q is

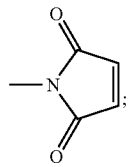

or (f) after step (b), reacting the compound of formula (HPP-B) with epichlorohydrin in a solvent to form the product, i.e. compound of formula (HPP-F) in which A is —O— and Q is

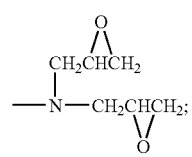

(g) after step (d), reacting the compound of formula (HPP-D) with maleic anhydride in a solvent to form the product, i.e. compound of formula (HPP-G) in which A is and Q is

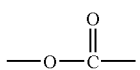

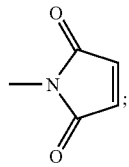

or (h) after step (d), reacting the compound of formula (HPP-D) with epichlorohydrin in a solvent to form the product, i.e. compound of formula (HPP-H) in which A is

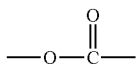

and Q is

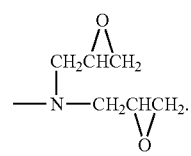

In the process of the present invention, for example, the compound of formula (III) in step (a) is 1-fluoro-4-nitrobenzene, and the compound of formula (III) in step (c) is 4-nitrobenzoyl chloride.

In the process of the present invention, the catalyst in step (a) is selected from the group consisting of compounds formed with elements of groups IA to VIIA, with an inorganic base and halide being preferred. For example, the catalyst is selected from the group consisting of cesium fluoride (CsF), potassium fluoride (KF), cesium chloride (CsCl), potassium chloride (KCl), potassium carbonate ($K_2CO_3$), sodium carbonate ($Na_2CO_3$), potassium hydroxide (KOH) and sodium hydroxide (NaOH).

In the process of the present invention, the solvents used in each step are conventionally known in the art. For example, the solvent used in step (a) is N—N-dimethylacetamide (DMAc), the solvent used in steps (b) and (d) is dimethylformamide (DMF), and the solvent used in step (c) is tetrahydrofuran (THF).

In another aspect, the present invention provides phosphorus-containing polyamides having the following chemical formula:

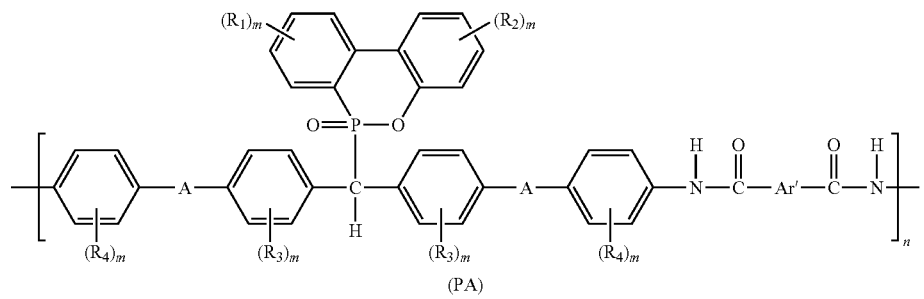

in which, A, $R_1$-$R_4$ and m are defined as above, Ar' is selected from the group consisting of

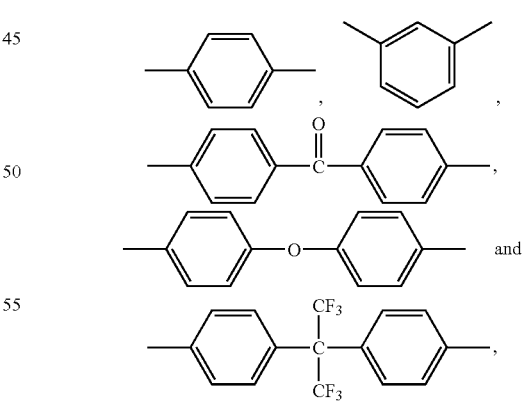

and n is an integer of 30-300.

The phosphorus-containing polyamide of formula (PA) can be used as a flexible printed circuit board material.

When A is —O—, $R_1$-$R_4$ are hydrogen atoms, and Ar' is phenyl, one embodiment of the polyamide of formula (PA) above can have a structural formula of

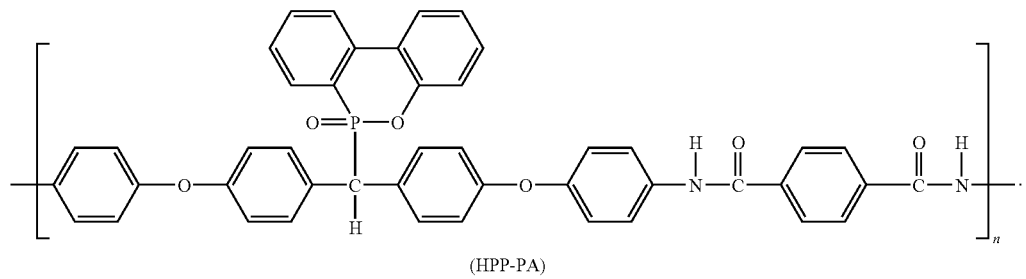

(HPP-PA)

The present invention provides a process of preparing the phosphorus-containing polyamide of formula (PA) as described above, which includes reacting the compound of formula (I) with a diacid compound of formula (IV) in a solvent to produce the phosphorus-containing polyamide of formula (PA), HOOC—Ar'.COOH (IV)

in which Ar' is selected from the group consisting of

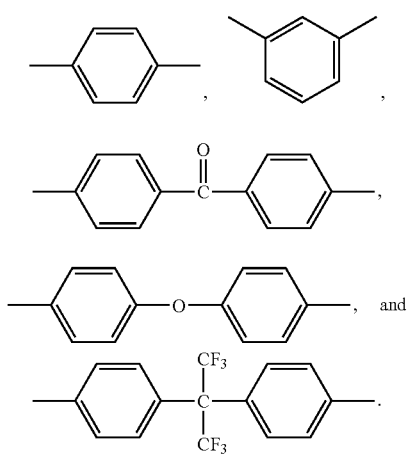

The solvent used in the process above is conventionally known in the art, and is, for example, N-methyl-pyrrolidone (NMP).

In the above process according to the present invention, calcium chloride or triphenyl phosphite (TPP) can be used to accelerate the polymerization. Furthermore, pyridine can also be used in the process above to facilitate the dehydration.

The present invention further provides phosphorus-containing polyimides having the following chemical formula:

in which A, $R_1$-$R_4$ and m are defined as above, Ar'' is selected from the group consisting of

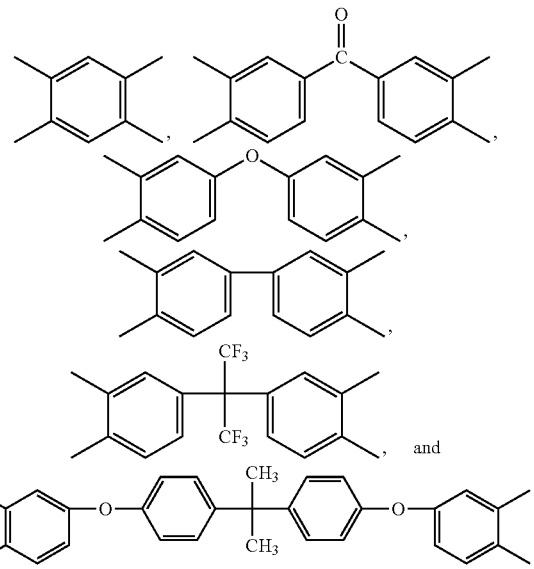

and n is an integer of 30-300.

The phosphorus-containing polyimide of formula (PI) can be used as a flexible printed circuit board material.

When A is —O—, $R_1$-$R_4$ are hydrogen atoms, and Ar'' is

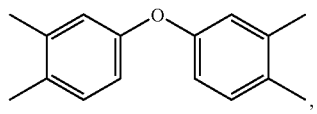

one embodiment of the polyimide of formula (PI) above can have a structural formula of

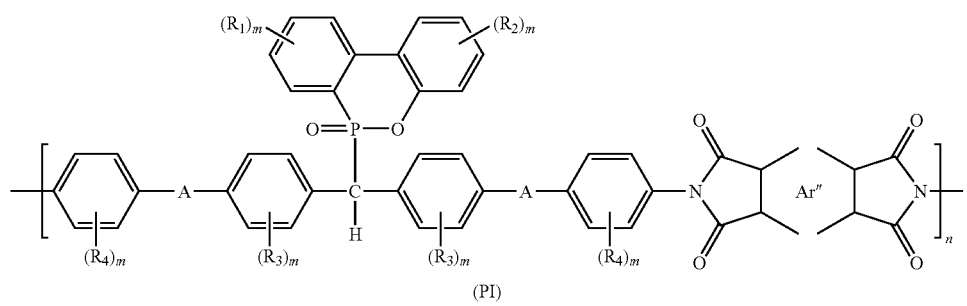

(PI)

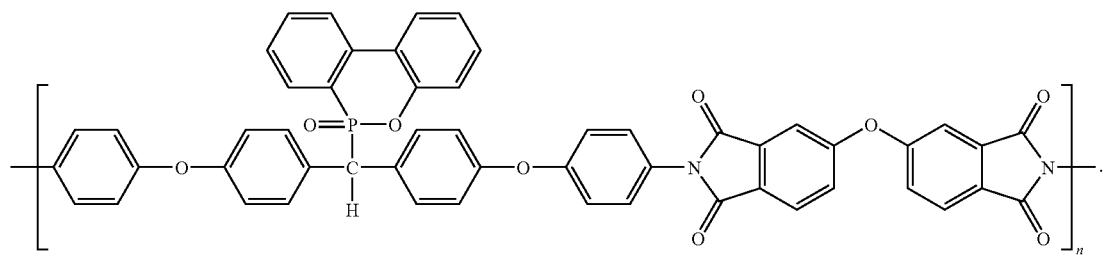
(HPP-PI)

The present invention also provides a process of preparing the phosphorus-containing polyimide of formula (PI) as described above, which includes reacting the compound of formula (I) above with a dianhydride compound of formula (V) in a solvent to produce the phosphorus-containing polyimide of formula (PI),

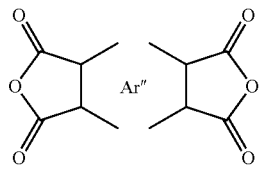
(V)

in which, Ar″ is selected from the group consisting of

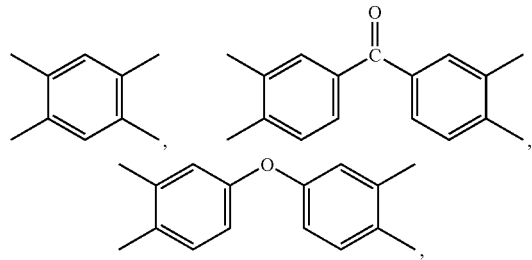

-continued

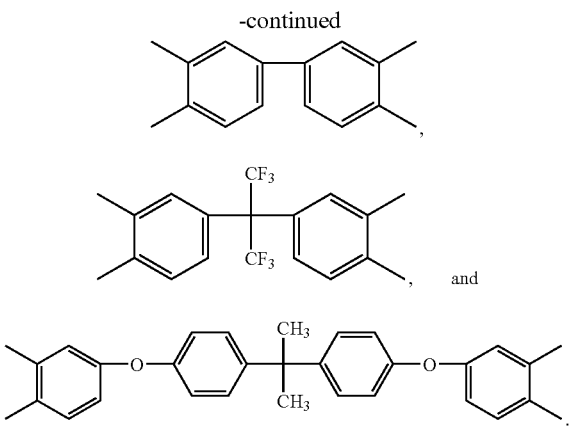

The solvent used in the process above is conventionally known in the art, and is, for example, m-cresol.

The following embodiments are used to further illustrate the present invention, but are not intended to limit the scope of the present invention. Any modifications and changes achieved by those skilled in the art without departing from the spirit of the present invention will fall within the scope of the present invention.

Specific embodiments of the implementation of the present invention described above can be represented by Scheme 1 below.

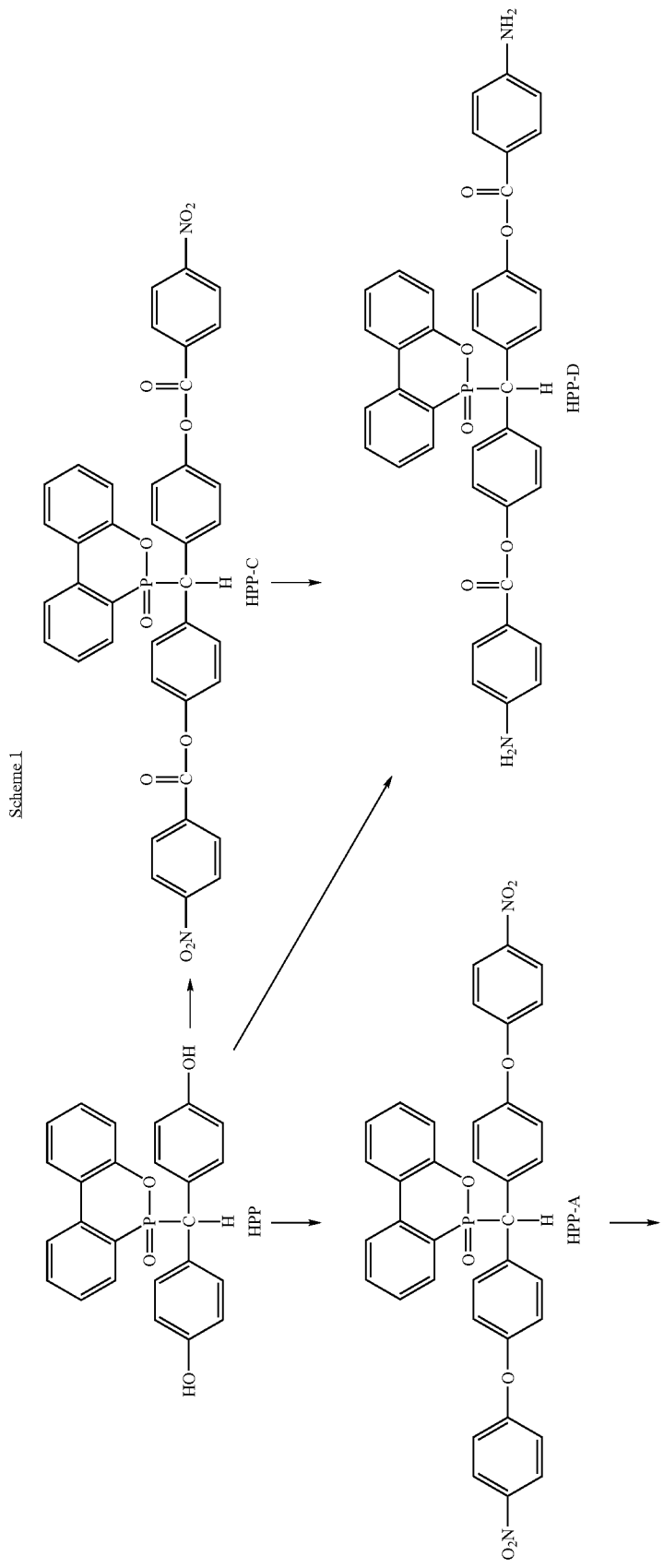

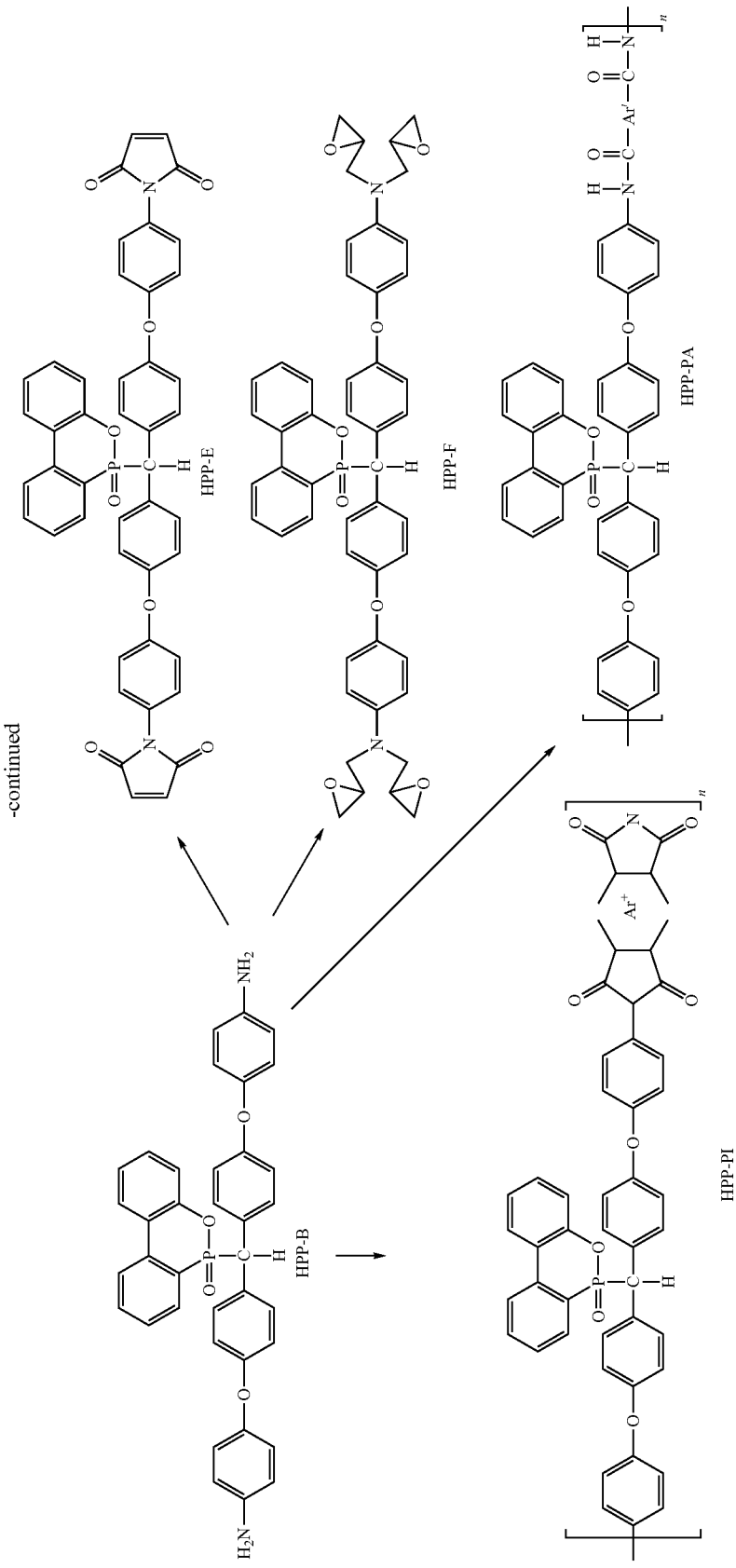

Example 1

Synthesis of Compound HPP-A

Monomer phosphorus-containing dinitrobenzene HPP-A was synthesized from starting material phosphorus-containing diphenol (HPP) and 1-fluoro-4-nitrobenzene in a solvent and in the presence of a catalyst, via the following steps.

8.2880 g (0.02 mol) of phosphorus-containing diphenol (HPP), 6.2085 g (0.044 mol) of 1-fluoro-4-nitrobenzene, 2.9025 g (0.021 mol) of potassium carbonate ($K_2CO_3$) and 80 g of N—N-dimethylacetamide (DMAc) were added to a 250 ml reactor.

Figure 2A:
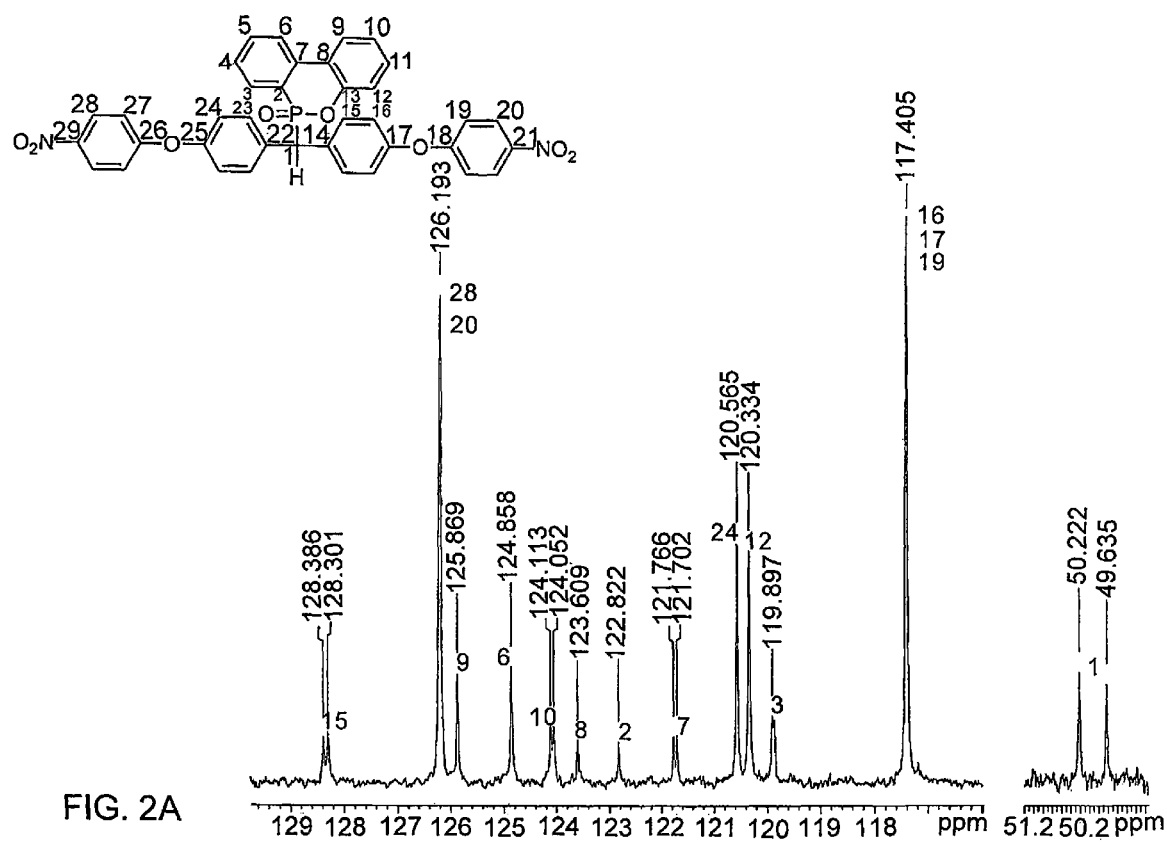
FIGS. 2A and 2B show $^{13}$C NMR spectra of compound HPP-A.
Figure 2B:
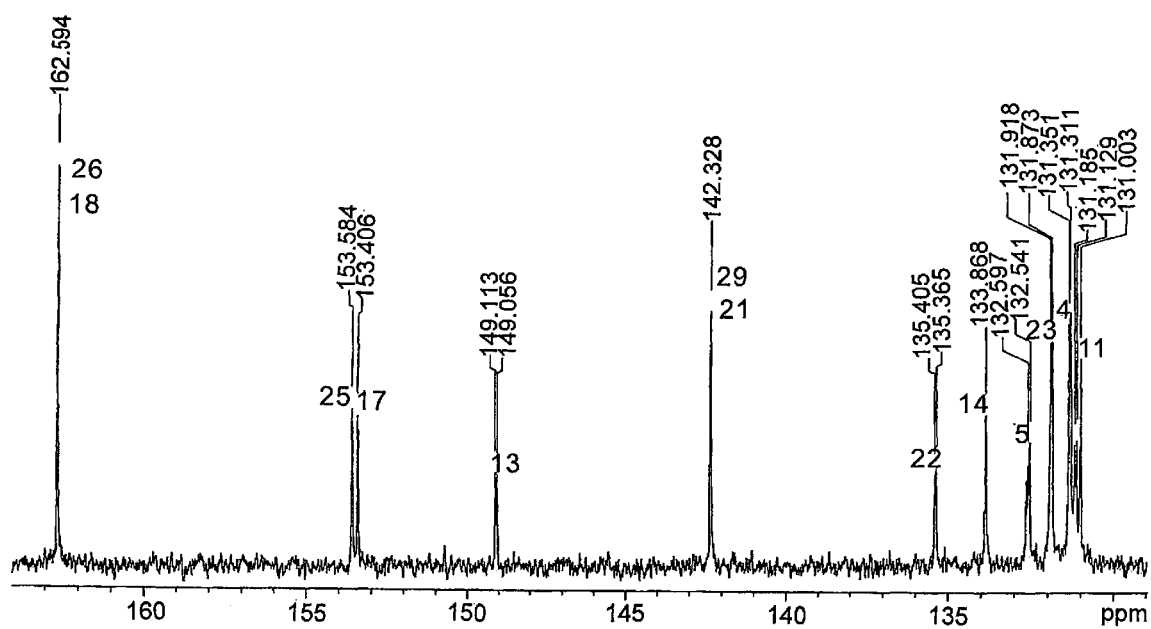

Next, the reaction temperature was raised to 80° C., and the reaction was continued for 24 h with stirring. The reactor was then cooled to room temperature, and the reactants were added dropwise to 1000 ml saturated saline and stirred to precipitate a light yellow solid, i.e. compound HPP-A. Afterwards, the synthesized compound HPP-A was filtered, washed with quantities of deionized water, and dried at 80° C. in a vacuum oven, to give 12.04 g of product HPP-A with a yield of 92%, which was then recrystallized with acetic anhydride to give 10.46 g of a light yellow product with a higher purity. The yield is 80%, and M.P. is 253° C. $^1$H NMR and $^{13}$C NMR spectra of the compound HPP-A are shown in FIGS. 1 and 2A and 2B respectively.

Example 2

Synthesis of Compound HPP-B

Monomer HPP-B was synthesized from starting material HPP-A and hydrogen in solvent DMF and in the presence of catalyst Pd/C, via the following steps.

Figure 3:
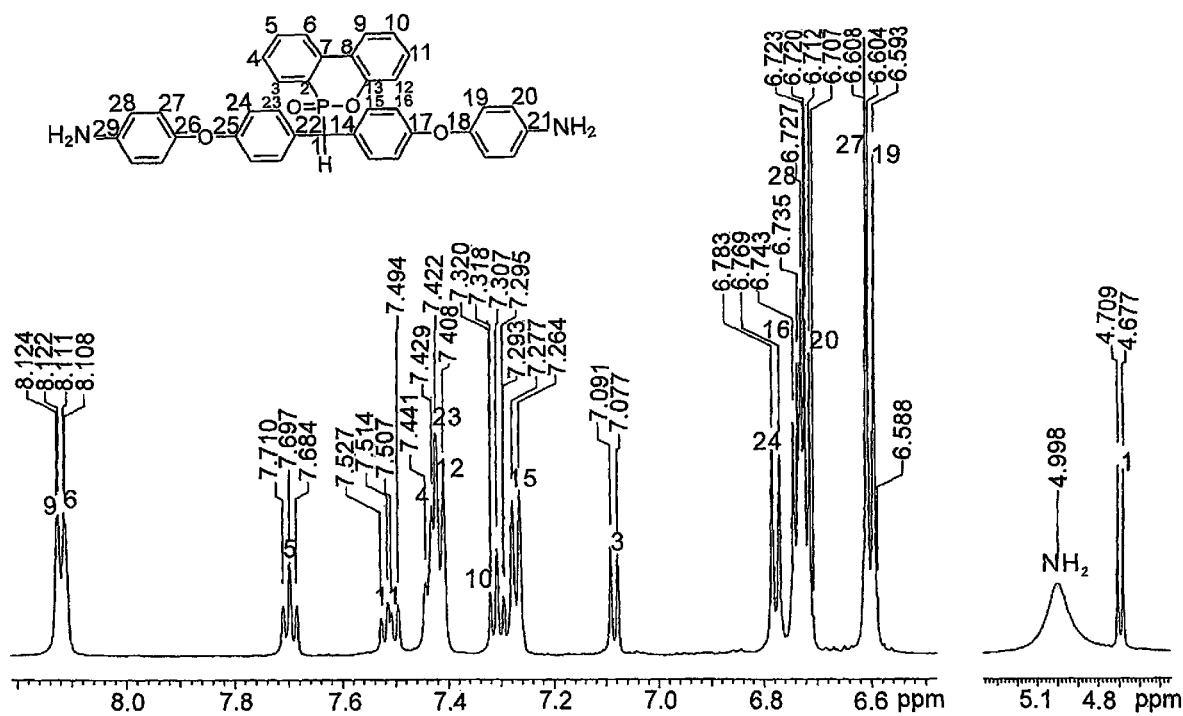
FIG. 3 is a $^1$H NMR spectrum of compound HPP-B.
Figure 4A:
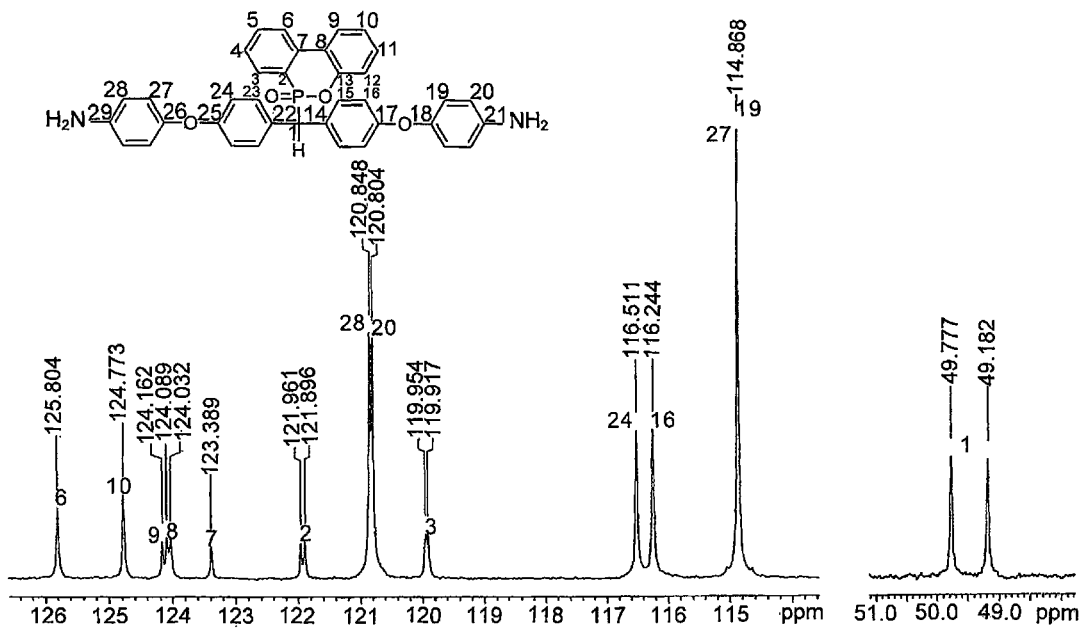
FIGS. 4A and 4B show $^{13}$C NMR spectra of compound HPP-B.
Figure 4B:
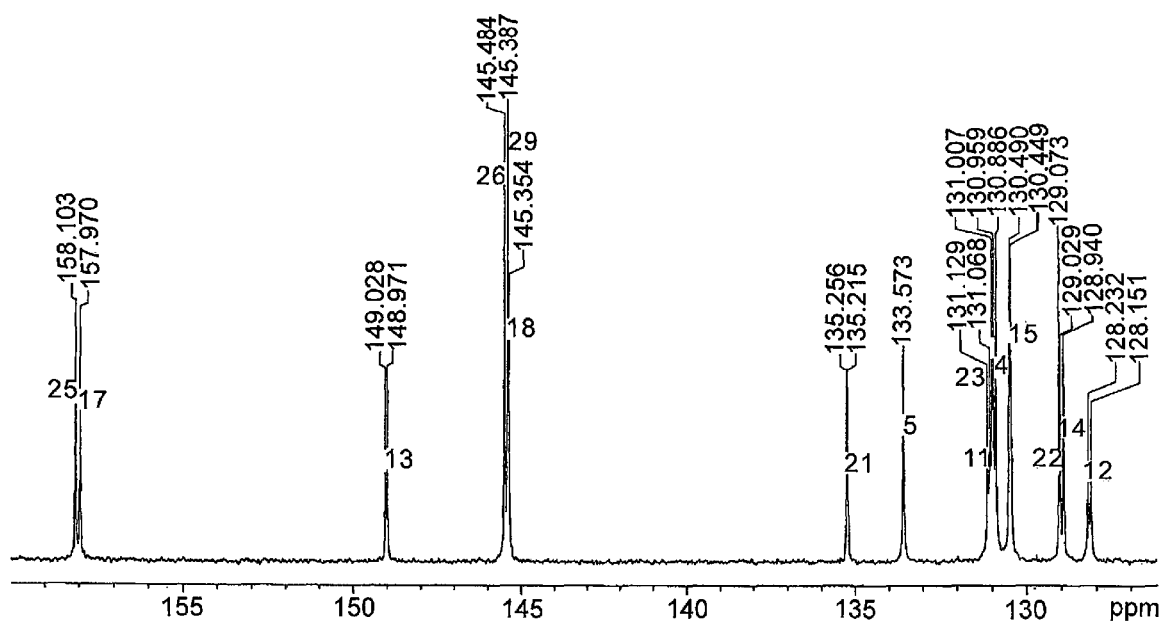

6 g of HPP-A, 0.10 g of Pd/C and 50 g of dimethylformamide (DMF) were first added to a 50 ml glass reactor and stirred. Purging and emptying were repeated three times with nitrogen and three times with hydrogen, and the reaction was continued for 12 h under a controlled pressure of 3.5 kg/cm$^2$. After reaction, Pd/C was filtered off, and the filtrate was added dropwise to 500 ml saturated saline to precipitate compound HPP-B, which was then washed with quantities of deionized water. After filtration, it was dried at 60° C., and weighed 5.07 g with a yield of 93%. Afterwards, it was dissolved into methanol with heating, filtered while hot, and then poured into deionized water to precipitate out, giving 3.75 g of a white product with a higher purity. The yield is 74%, and M.P. is 104° C. $^1$H NMR and $^{13}$C NMR spectra of HPP-B are shown in FIGS. 3 and 4A and 4B respectively.

Example 3

Synthesis of Compound HPP-C

Compound HPP-C was synthesized via the following steps.

41.00 g (0.10 mol) of HPP and 200 ml of THF were added to a 500 ml reactor and stirred until dissolved. 22.00 g (0.22 mol) of triethylamine were added and the reactor was cooled to 10° C., then 41.00 g (0.22 mol) of 4-nitrobenzoyl chloride were dissolved into 80 ml of THF, poured into a feeding funnel, and slowly added dropwise to the reactor in 2 h. The reaction was continued at a controlled temperature of 20° C. for 2 h, and then the product was filtered and recrystallized with glacial acetic acid to give a yellow DOPO derivative, HPP-C.

Example 4

Synthesis of Compound HPP-D

Monomer HPP-D was synthesized from starting material HPP-C and hydrogen in solvent DMF and in the presence of catalyst Pd/C, via the following steps.

6 g of HPP-C, 0.10 g of Pd/C and 50 g of DMF were first added to a 50 ml glass reactor and stirred. Purging and emptying were repeated three times with nitrogen and three times with hydrogen, and the reaction was continued for 8 h under a controlled pressure of 7 kg/cm$^2$. After reaction, Pd/C was filtered off, and the filtrate was added dropwise to 500 ml deionized water to precipitate compound HPP-D, which was then filtered and dried at 100° C., to give a pure white product HPP-D.

Example 5

Synthesis of Compound HPP-E

Compound HPP-E was synthesized via the following steps.

29.83 g (0.05 mol) of HPP-B, 9.81 g (0.1 mol) of maleic anhydride and 200 ml of acetone were added to a 500 ml reactor, and reacted for 4 h in an ice bath. Next, 50 ml of acetic anhydride and 8.50 g of sodium acetate were added, warmed to 60° C. and reacted for 4 h, followed by solvent removal by distillation under reduced pressure, precipitation with ethanol, and then recrystallization with ethanol, to give a pure compound HPP-E.

Example 6

Synthesis of Compound HPP-F

Compound HPP-F was synthesized via the following steps.

300 g of HPP-B and 1000 g of epichlorohydrin were added to a 3 L reactor, and stirred under normal pressure until a homogeneously mixed solution was formed. The reaction temperature was raised to 70° C. under an absolute pressure of 190 mmHg, and 80.20 g of a 49% sodium hydroxide solution was added portionwise in 4 h while water in the reactor was removed by azeotropic distillation. After reaction, epichlorohydrin and solvent were distilled out by distillation under reduced pressure, the product was dissolved into methyl ethyl ketone and deionized water, sodium chloride in the resin was washed off with water, and then the solvent was distilled out by distillation under reduced pressure, to give a light yellow epoxy-containing DOPO derivative HPP-F with an epoxy equivalent of 217 g/eq.

Example 7

Synthesis of Polymer HPP-PA

Phosphorus-containing polyamide HPP-PA was synthesized with diamine based monomer (HPP-B) via the following steps.

0.7458 g (1.25 mmol) of diamine monomer HPP-B, 0.2079 g mmol) of terephthalamic acid, 0.3 g of calcium chloride ($CaCl_2$), 0.9 ml of triphenyl phosphite (TPP), 1.2 ml of pyridine, and 5 ml of N-methyl-pyrrolidone (NMP) were added to a 100 ml three-necked flask purged with nitrogen for 30 min, and stirred. After reaction for 4 h at an elevated temperature of 100° C., the reaction was cooled to room temperature, and the resulting polymer solution was slowly added dropwise into 300 ml of methanol to precipitate out. The fibrous precipitate produced was filtered, washed with methanol and hot water, collected and dried at 150° C., to give 0.8973 g a product. Next, the synthesized polyetheramide polymer was dissolved into DMAc or NMP to a solid content of about 20%, and then the polyamide solution was coated onto a glass substrate with a coater, to form a film of about 45 μm in thickness. It was heated and treated for 12 h at 80° C. in a hot air circulating oven to remove most of the solvent, and then further treated for 2 h at an elevated temperature of 200° C. Finally, it was soaked in water to separate the HPP-PA film from the glass substrate. The glass transition temperature was determined to be 246° C. by DSC.

Example 8

Synthesis of Polymer HPP-PI

Phosphorus-containing polyimide HPP-PI was synthesized with monomer HPP-B via the following steps.

Figure 5:
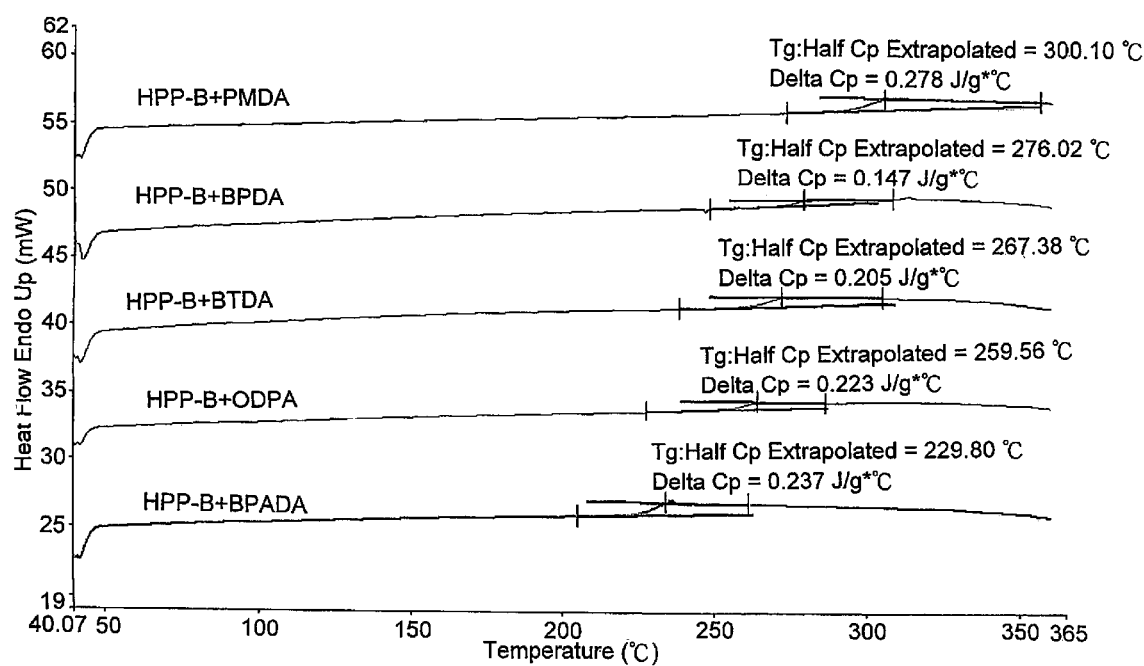
FIG. 5 shows a DSC analytic diagram of polymer HPP-PI.

0.8949 g (1.5 mmol) of diamine monomer HPP-B, 0.4653 g (1.5 mmol) of 4,4'-oxydiphthalic anhydride (ODPA) and 7.8 g of m-cresol was stirred in a 100 ml three-necked flask, then the reaction temperature was raised to 200° C., and the reaction was continued for 2 h. Next the reactants were poured into methanol to precipitate out, and after being filtered, the product was washed for 24 h with hot methanol, filtered and dried at 100° C. to give 1.2310 g of a product. The dried product was dissolved into DMF to a solid content of about 20%, and then the polyimide solution was coated onto a glass substrate with a coater, to form a film of about 20 μm in thickness. It was heated and treated for 12 h at 80° C. in a hot air circulating oven to remove most of the solvent, and then further treated for 2 h at an elevated temperature of 200° C., to give a pale colored polyimide. The glass transition temperature was determined to be 259° C. by DSC. FIG. 5 shows a DSC analytic diagram of the polymer HPP-PI.

The following claims are used to define the reasonable scope of the present invention. It should be appreciated that any obvious modifications achieved by those skilled in the art on the basis of the disclosure of the present invention should also fall within the reasonable scope of the present invention.

We claim:

1. A phosphorus-containing compound of general formula (I):

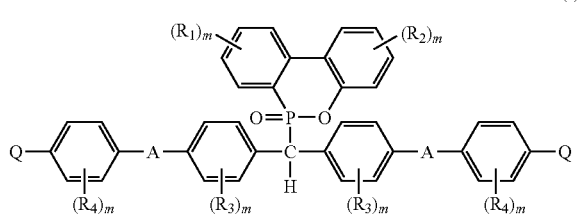

(I)

wherein $R_1$-$R_4$ are each selected from the group consisting of hydrogen atom, $C_1$-$C_6$alkyl, $C_1$-$C_6$alkoxy, $C_1$-$C_6$haloalkyl, $C_3$-$C_7$cycloalkyl, —$CF_3$, —$OCF_3$, and halogen atom;

A is —O— or

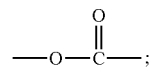

Q is selected from the group consisting of —$NO_2$, —$NH_2$,

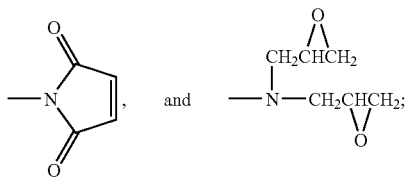

and m is an integer of 1-4, with the proviso that the compound is not (HPP-B)

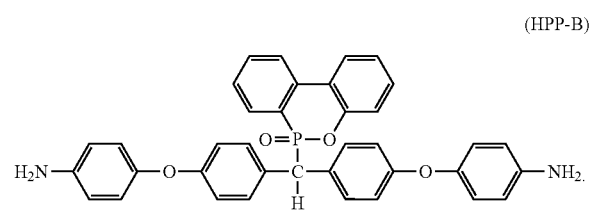

2. The compound of formula (I) according to claim 1, wherein each of $R_1$-$R_4$ is hydrogen atom, (a) when A is —O— and Q is —$NO_2$, the compound of formula (I) is of formula (HPP-A);

(HPP-A)

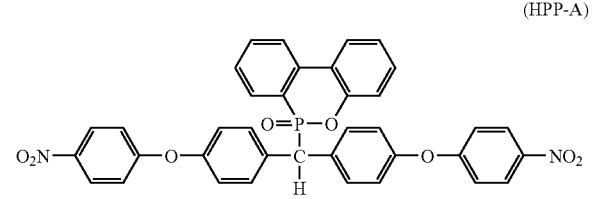

(b) when A is

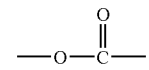

and Q is —$NO_2$, the compound of formula (I) is of formula (HPP-C);

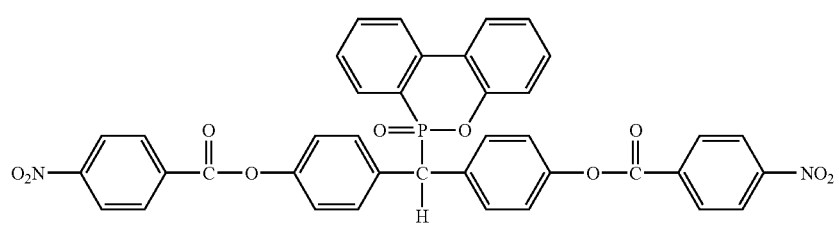
(HPP-C)
(c) when A is
and Q is —NH$_2$, the compound of formula (I) is of formula (HPP-D);
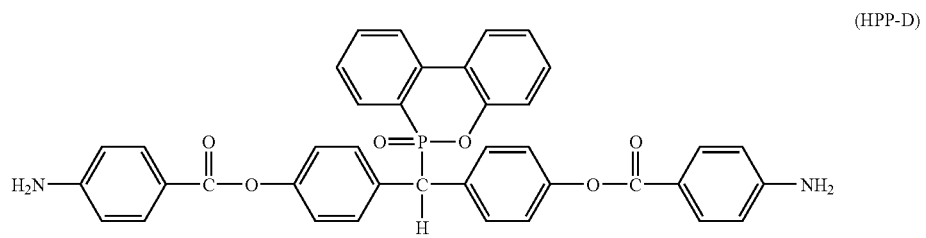
(HPP-D)
(d) when A is —O— and Q
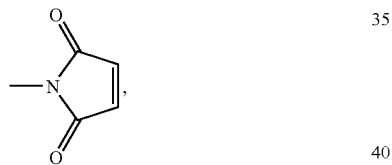
is the compound of formula (I) is of formula (HPP-E);
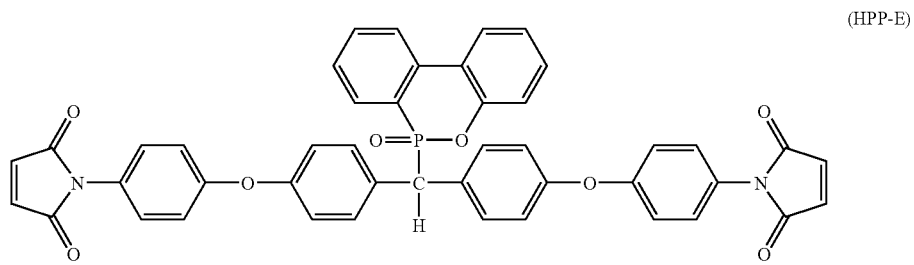
(HPP-E)
(e) when A is —O— and Q is
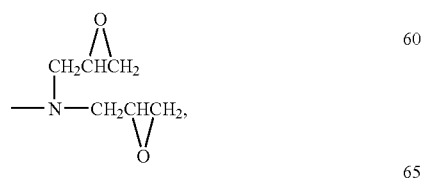
the compound of formula (I) is of formula (HPP-F);

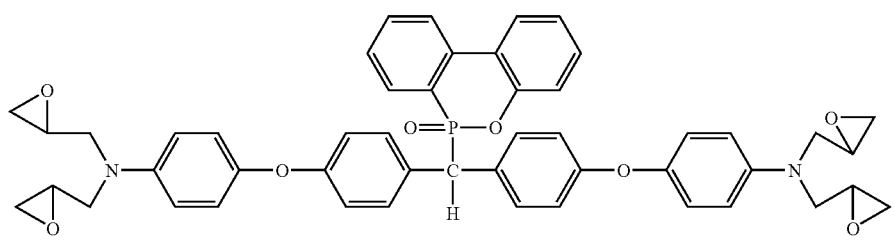
(f) when A is
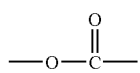
and Q is
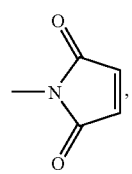
the compound of formula (I) is of formula (HPP-G); or
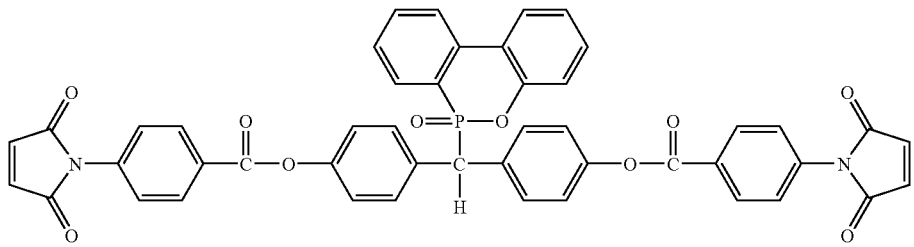
(g) when A is
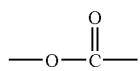
and Q is
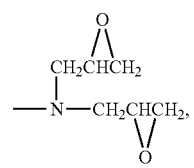
the compound of formula (I) is of formula (HPP-H)

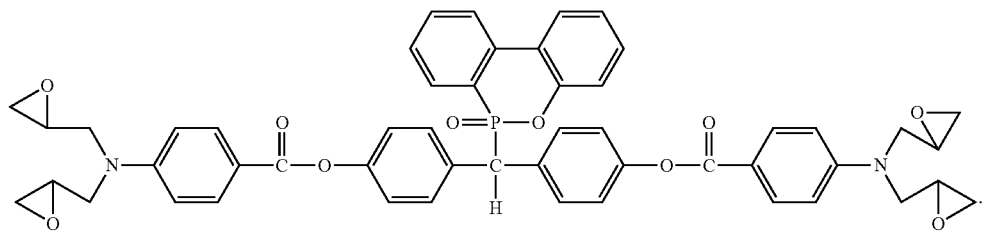
(HPP-H)
* * * * *